US00PP20999P2

(12) United States Plant Patent
Whetman

(10) Patent No.: US PP20,999 P2
(45) Date of Patent: May 18, 2010

(54) ***DIANTHUS* PLANT NAMED 'STARDUST'**
(50) Latin Name: *Dianthus×hybrida*
Varietal Denomination: Stardust

(76) Inventor: John Whetman, Deerpark Farm, Chudleigh, Newton Abbey, Devon (GB) TQ13 0NH ( * ) Notice: Subject to any disclaimer, the term of this patent is extended or adjusted under 35 U.S.C. 154(b) by 0 days.

(21) Appl. No.: 12/228,983

(22) Filed: Aug. 18, 2008

(51) Int. Cl.
*A01H 5/00* (2006.01)

(52) U.S. Cl. ..... Plt./272
(58) Field of Classification Search ..... Plt./272
See application file for complete search history.

*Primary Examiner*—Annette H Para

(57) ABSTRACT

A new cultivar of *Dianthus* plant named 'STARDUST' that is characterized by compact habit, grey-green foliage, and double flowers that are pale coral in color. In combination these traits set 'STARDUST' apart from all other existing varieties of *Dianthus* known to the inventor.

2 Drawing Sheets

Genus: *Dianthus.*
Species: ×*hybrida.*
Denomination: 'STARDUST'.

BACKGROUND OF THE INVENTION

This application claims the benefit of priority under 35 U.S.C. 119(f) of the earlier application for European Community Plant Breeders Rights, Application Number 2007/2058 filed Sep. 19, 2007.

The present invention relates to a new and distinct cultivar of *Dianthus* that is grown for use as a flowering plant for pots and containers and as a hardy perennial for the garden and landscape. The new cultivar is known botanically as *Dianthus×hybrida* and will be referred to hereinafter by the cultivar name 'STARDUST'.

'STARDUST' is a complex hybrid plant that is the product of a long term breeding program conducted in a greenhouse environment in Houndspool, Dawlish, Devon, United Kingdom. The primary focus of the breeding program is to produce new cultivars of *Dianthus* that exhibit unique growth habit and flower colors. The inventor selected 'STARDUST' in 2004 for its double flowers that are pale coral in color.

'STARDUST' resulted from the controlled pollination between an unreleased and unpatented *Dianthus* previously raised by the inventor and known by its code name *Dianthus* 'SUW03.08' as female parent plant, and an unreleased and unpatented *Dianthus* previously raised by the inventor and known by its code name *Dianthus* '00.16' as male parent plant.

'STARDUST' is distinguishable from both of its parents by having smaller flowers and greyer, more glaucous foliage.

The variety of *Dianthus* which is considered by the inventor to most closely resemble 'STARDUST' is the inventor's variety *Dianthus* 'Devon Winnie' (U.S. Plant Pat. No. 14,893). Whereas the flowers of 'STARDUST' and 'Devon Winnie' are both double, those of 'Devon Winnie' are slightly smaller (ranging from 25 mm to 35 mm in diameter) and are dark pink in color.

Asexual reproduction of the new cultivar was first accomplished by the inventor in 2004 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'STARDUST'. These traits in combination distinguish this cultivar from all other commercial varieties known to the inventor. 'STARDUST' has not been tested under all possible conditions and phenotypic differences may be observed with variations in environmental, climatic and cultural conditions, however, without any variance in genotype.

1. 'STARDUST' exhibits a compact habit.
2. 'STARDUST' blooms profusely.
3. 'STARDUST' exhibits double flowers that are a pale coral in color.
4. 'STARDUST' blooms from March through October.
5. 'STARDUST' exhibits grey-green foliage.
6. At maturity, the height of the foliage mound of 'STARDUST' is 13 cm to 17 cm, and the width of the foliage mound is 17 cm to 20 cm.
7. 'STARDUST' is perennial and is hardy to −15° C.
8. 'STARDUST' is suitable for use as a flowering plant in pots and containers.

BRIEF DESCRIPTION OF THE DRAWINGS

The accompanying color drawings illustrate the overall appearance of the new *Dianthus* variety 'STARDUST' showing colors as true as it is reasonably possible to obtain in colored reproductions of this type. Colors in the drawings may differ from the color values cited in the detailed botanical description, which accurately describe the actual colors of the new variety 'STARDUST'.

The drawing labeled as FIG. 1 depicts an entire flowering plant.

Figure 1:
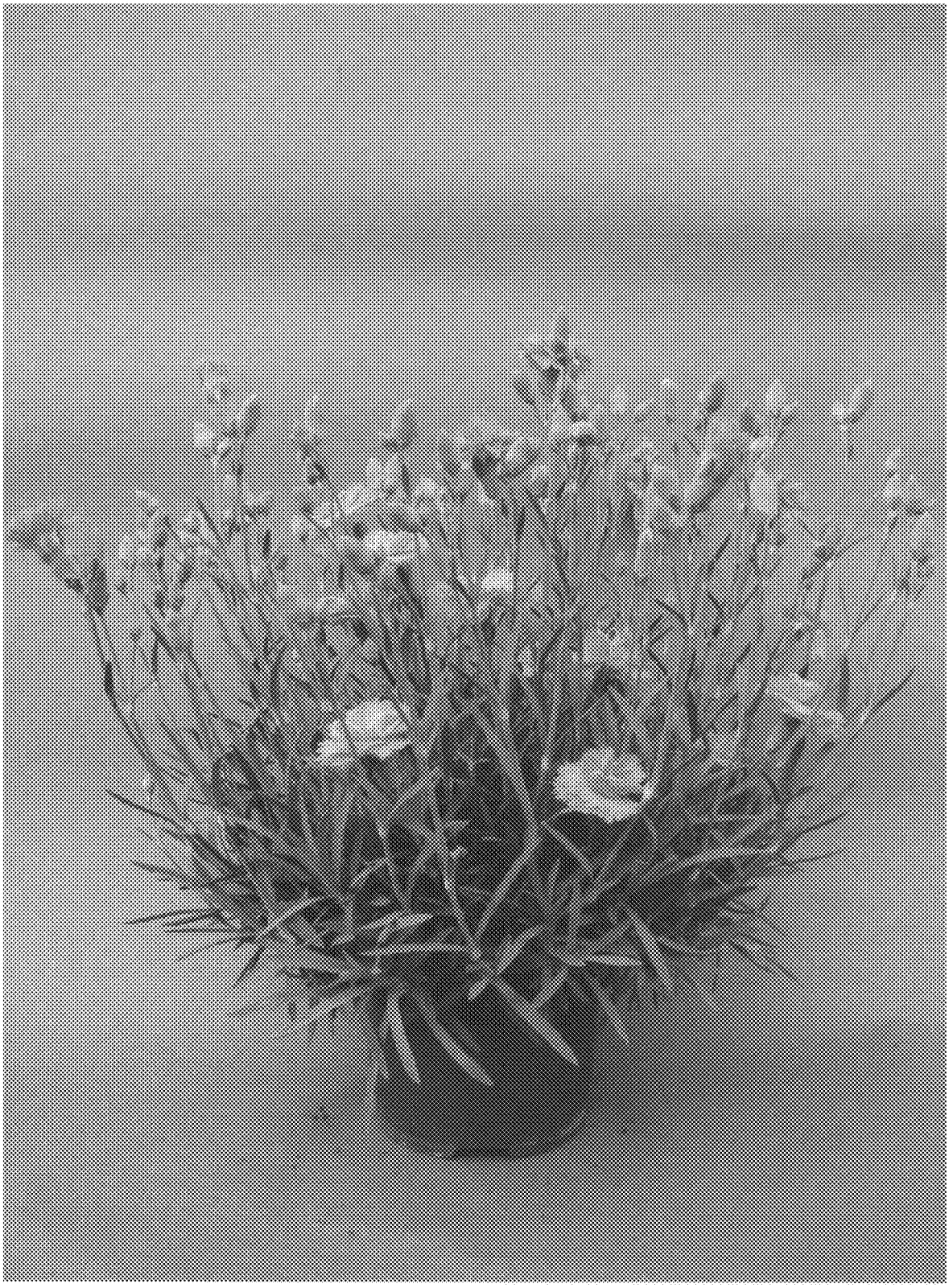
Figure 2:
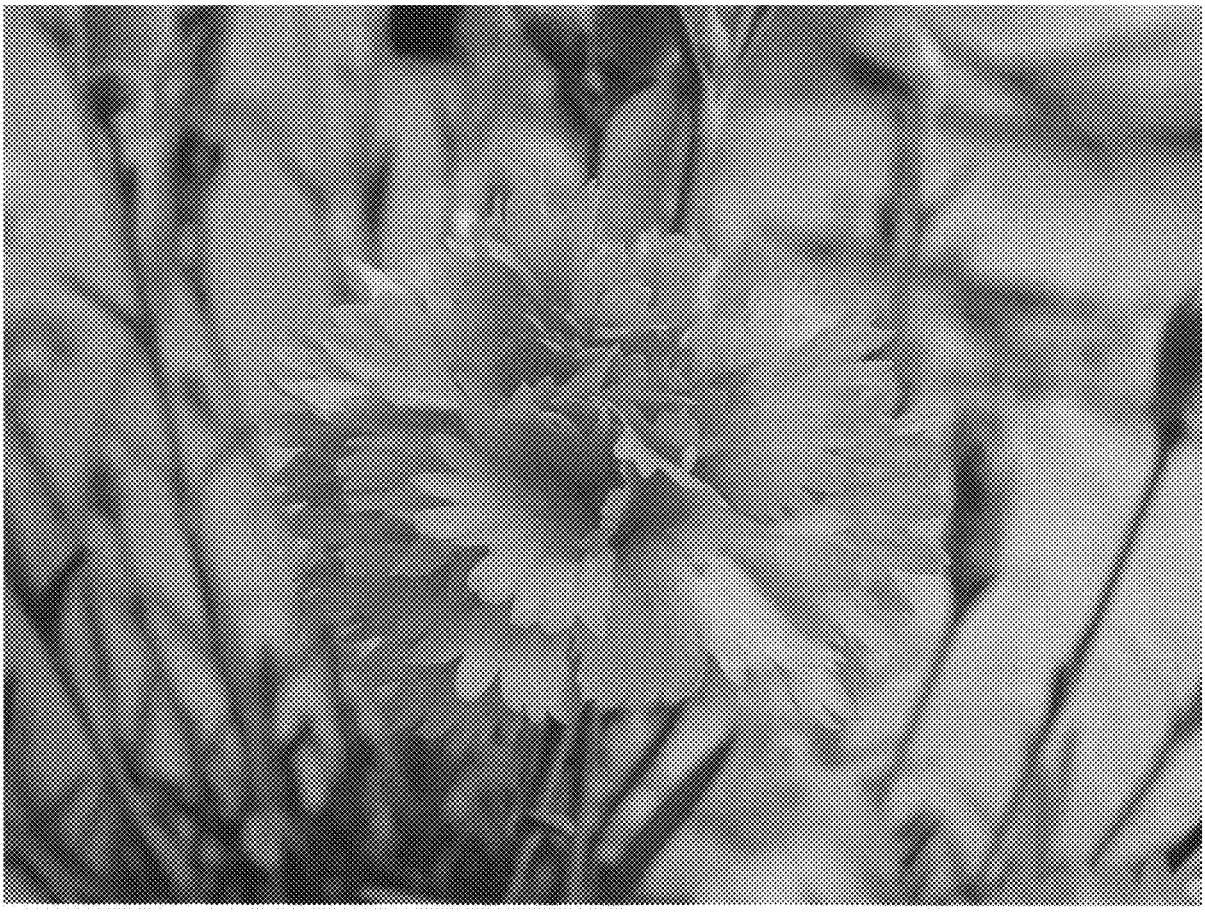

All drawings were made of 9 months old plants which have grown in 1.5-litre containers in a cold (unheated) glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'STARDUST'. Data was collected in spring from 9 months old plants which have been grown in 1.5-litre containers in spring, and grown in an unheated glasshouse in Devon, United Kingdom. The color determinations are in accordance with the 2007 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification: *Dianthus* 'STARDUST'.

Species: ×*hybrida*.

Common name: Garden pink.

Commercial classification: *Dianthus* hybrid.

Type: Perennial.

Use: Used as a flowering plant for pots and containers and for planting in the garden or landscape.

Parentage: 'STARDUST' is a complex hybrid plant that resulted from the induced open pollination between the following parent plants:

*Female parent plant.*—*Dianthus* 'SUW03.08'.

*Male parent plant.*—*Dianthus* '00.16'.

Plant description:

*Bloom period.*—March through October.

*Plant habit.*—Compact mound with many branches and stems; upright growth.

*Plant height.*—13 cm to 17 cm after 9 months.

*Plant width.*—17 cm to 20 cm after 9 months.

*Plant hardiness.*—Hardy to minus 15° Centigrade.

*Root system.*—Fine fibrous roots.

*Propagation.*—Propagation is accomplished using vegetative cuttings.

*Cultural requirements.*—Grow in full sun, with moderate water, and well-drained moderately fertile soil. Remove dead flower heads to maintain flowering.

*Diseases and pests.*—Susceptible to known *Dianthus* pests and disease but no other susceptibilities to pests or disease are known to the inventor.

*Time and temperature needed to produce a rooted cutting.*—3 weeks are needed to produce roots on cuttings using a mist propagation unit with bottom heat of 21° Centigrade, and a minimum air temperature of 15° Centigrade.

*Crop time.*—3 months starting in the early spring through summer and 6 months starting in the fall is needed to produce a finished container size plant from a well-rooted cutting.

Stem:

*Shape.*—Cylindrical.

*Stem dimensions.*—7 cm to 10 cm in height and 3 mm in diameter.

*Stem surface.*—Glabrous and glaucous.

*Stem color.*—145C.

*Branching.*—Numerous shoots from the axils of the lower leaves.

*Internode length.*—10 mm to 20 mm between nodes.

*Node color.*—145C.

*Node dimensions.*—4 mm in length and 2 mm in diameter.

Foliage:

*Type.*—Evergreen.

*Shape.*—Linear and straight.

*Division.*—Simple.

*Apex.*—Acute.

*Base.*—Decurrent.

*Venation.*—Not Prominent.

*Margins.*—Entire.

*Attachment.*—Sheathing.

*Arrangement.*—Opposite.

*Surfaces* (*adaxial and abaxial*).—Glaucous.

*Leaf dimensions.*—50 mm to 75 mm in length and 5 mm in width.

*Leaf color* (*adaxial and abaxial surfaces*).—N138A.

*Fragrance.*—Absent.

Flowers:

*Inflorescence.*—Cymose.

*Number of flowers per stem.*—From 3 to 5.

*Peduncle dimensions.*—110 mm to 150 mm in length and 2 mm in width.

*Peduncle strength.*—Erect.

*Peduncle color.*—133B.

*Flower development.*—In sequence from the uppermost bud.

*Flower type.*—Salviform, double and symmetrical.

*Flower shape.*—Circular.

*Flower profile.*—Reflexed.

*Flower dimensions* (*including calyx*).—35 mm in length and 35 mm in diameter.

*Fragrance.*—Medium.

*Petals.*—Number: 15–20 petals. Profile, upper part of corolla: Convex. Profile, lower part of corolla: Concave. Arrangement: Persistent, double, apopetalous, overlapping. Margin: Crenate-dentate with indentations 2 mm to 3 mm deep. Texture: Soft. Shape: Obdeltoid. Surface: Glabrous. Dimensions: 30 mm to 35 mm in length and 20 mm to 25 mm in width. Color (adaxial surface): Ground color of blade: Between 52B and 52C. Band across blade: 52A. Middle of strap: 145C Base of strap: 145D. Color (abaxial surface): Ground color of blade: 62C. Band across blade: Absent. Middle of strap: 145C. Base of strap: 145D.

*Calyx.*—Shape: Cylindrical. Longitudinal profile: Flat. Dimensions: 18 mm to 20 mm in length and 8 mm in diameter. Sepals: Fused. Number of sepals: 5. Sepal surface: Glaucous. Sepal color (both surfaces): N138C. Anthocyanin: Absent. Splitting: Not observed.

*Epicalyx.*—Bracts: 1 pair of 2. Shape of outer lobe: Acuminate. Dimensions: 7 mm in length and 6 mm in width. Color: 136D in the middle and 143B on the border. Anthocyanin: Absent.

*Bracteoles.*—Number: 2. Dimensions: 7 mm in length and 4 mm in width. Color: 136D in the middle and 143B on the border. Anthocyanin: Not present.

*Lastingness of flower.*—Each individual flower lasts an average of 10 days at 20° C. on the plant.

Reproductive organs:

*Stamens.*—Number: 5. Filament color: NN155D. Dimensions: 10 mm to 15 mm in length and 0.5 mm in diameter.

*Anthers.*—Number: 5. Color: NN155D. Dimensions: 1 mm to 2 mm in length and 0.5 mm in diameter. Attachment: Basifixed.

*Pollen.*—Absent.

*Style.*—Number: 2. Shoulder: Absent. Color: NN155D. Dimensions: 25 mm to 30 mm in length and 0.5 mm in width.

*Stigma.*—Number: Single. Color: 63B. Dimensions: 5 mm to 8 mm above petals.

*Ovary.*—Position: Superior. Dimensions: 5 mm in length and 4 mm in diameter. Shape: Spindle. Color (adaxial): 144A. Color (abaxial): 145B.

Seed: Sterile, the seeds are aborted before they became mature.

The invention claimed is:

1. A new and distinct cultivar of *Dianthus* plant named 'STARDUST' as described and illustrated herein.

* * * * *